United States Patent [19]

Grisar et al.

[11] 4,371,737

[45] Feb. 1, 1983

[54] 5-AMINOMETHYL-2,3-DIHYDRO-2-OXO-1H-IMIDAZOLE-4-CARBOXYLIC ACID DERIVATIVES

[75] Inventors: J. Martin Grisar; Richard A. Schnettler; Richard C. Dage, all of Cincinnati, Ohio

[73] Assignee: Merrell Dow Pharmaceuticals Inc., Cincinnati, Ohio

[21] Appl. No.: 260,445

[22] Filed: May 4, 1981

[51] Int. Cl.³ .................. C07D 241/04; C07D 233/04
[52] U.S. Cl. .................................. 544/370; 544/139; 546/210; 546/278; 548/321
[58] Field of Search ................................ 544/370, 360

[56] References Cited

U.S. PATENT DOCUMENTS

| 2,441,933 | 7/1945 | Duschinsky | 548/321 |
| 2,514,380 | 12/1926 | Duschinsky | 548/321 |
| 3,303,199 | 2/1967 | Doebel et al. | 544/370 |
| 3,895,934 | 7/1975 | Linder et al. | 71/121 |

FOREIGN PATENT DOCUMENTS 3021792  1/1981  Fed. Rep. of Germany ...... 544/370

OTHER PUBLICATIONS

Boularand et al., Chimie Ther., 8, 638 (1973).
Duschinsky et al., J. Am. Chem. Soc., 68, 2350 (1946).
Duschinsky et al., J. Am. Chem. Soc., 70, 657 (1948).
Dage et al., Fed. Proc., 39, 1105 (1980) (abstract).

Primary Examiner—Donald G. Daus
Assistant Examiner—Sharon A. Gibson
Attorney, Agent, or Firm—John J. Kolano; Gary D. Street; Raymond A. McDonald

[57] ABSTRACT

2,3-Dihydro-2-oxo-1H-imidazole-4-carboxylic acid derivatives having a (substituted amino)methyl substituent at the 5-position, are useful as cardiotonics, antihypertensives and antithrombotic agents. The compounds are obtained by the reaction of an appropriate amine with a 5-(bromomethyl)-2,3-dihydro-2-oxo-1H-imidazole-4-carboxylic acid ester or amide.

5 Claims, No Drawings

5-AMINOMETHYL-2,3-DIHYDRO-2-OXO-1H-IMIDAZOLE-4-CARBOXYLIC ACID DERIVATIVES

The present invention relates to imidazole-4-carboxylic acid derivatives having an aminomethyl substituent at the 5-position. More particularly, it relates to compounds having the following general formula:

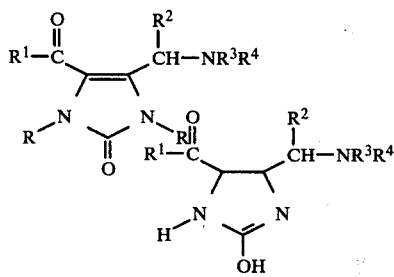

wherein R is hydrogen, lower alkyl of 1–4 C, lower alkanoyl of 2–4 C, or benzoyl; $R^1$ is hydroxy, lower alkoxy of 1–4 C, amino, (lower alkyl)amino, (lower alkyl)$_2$amino or —$NHR_5$ wherein $R_5$ is phenyl, methylphenyl, dimethylphenyl or methoxyphenyl; $R^2$ is hydrogen or lower alkyl of 1–4 C; and —$NR^3R^4$ is (lower alkyl)$_2$amino, 1-pyrrolidinyl, 1-piperidinyl, 4-morpholinyl,

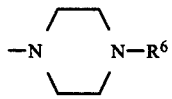

wherein $R^6$ is lower alkyl of 1–4 C, phenyl, halophenyl, methylphenyl, methoxyphenyl or trifluoromethylphenyl; and pyridinium chloride. The present invention further encompasses the pharmaceutically acceptable acid addition salts and the lower alkyl quaternary ammonium salts of the aforesaid compounds which are not already quaternized.

The lower alkyl groups referred to above contain 1 to 4 carbon atoms. Examples of such lower alkyl groups are methyl, ethyl, propyl, isopropyl and butyl. The lower alkanoyl groups referred to above contain 2 to 4 carbon atoms and can be exemplified by acetyl, propionyl and butyryl. Examples of lower alkoxy are methoxy, ethoxy and propoxy. Examples of the halophenyl groups referred to above include fluorophenyl, chlorophenyl and bromophenyl. When —$NR^3R^4$ is pyridinium chloride, the group consists of pyridine with a free valence on the nitrogen for attachment of the group to the remainder of the molecule. The pyridine nitrogen is thus quatenary so that the group must also contain an anion, preferably chloride.

Illustrative of the pharmaceutically acceptable acid addition salts of the compounds of the present invention are salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid. Illustrative of quaternary ammonium salts are those formed with lower alkyl halides such as methyl bromide, methyl iodide, ethyl bromide and ethyl iodide.

Where R is hydrogen in the compounds of the present invention, several tautomeric forms of the compounds are possible as follows:

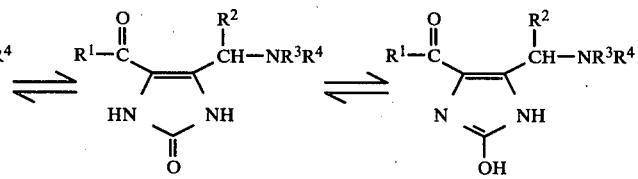

wherein the various groups are as defined earlier. These tautomers are acidic and can react with strong bases to form pharmaceutically acceptable salts of the following formulas:

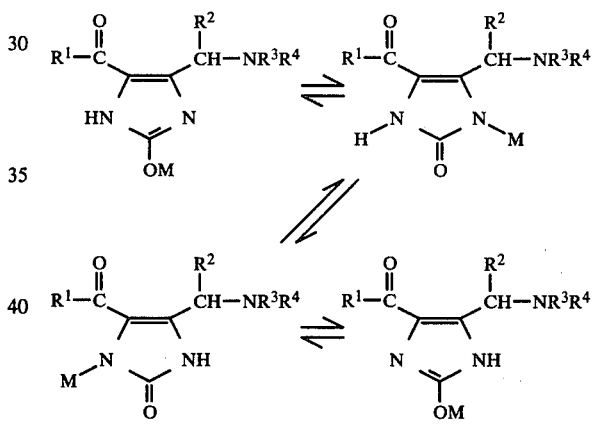

wherein the various groups are defined as above and M is a pharmaceutically acceptable alkali metal such as sodium or potassium. Throughout this disclosure, the term 2-oxo-1H-imidazole shall be taken to mean any of the tautomers or the tautomer salts as set forth above.

As examples of compounds of the present invention are the following:
Ethyl 5-[[4-(4-chlorophenyl)-1-piperazinyl]methyl]-2,3-dihydro-2-oxo-1H-imidazole-4-carboxylate.
N,N-diethyl-5-[[4-(2-methylphenyl)-1-piperazinyl]methyl]-2,3-dihydro-2-oxo-1H-imidazole-4-carboxamide.
Methyl 5-[[4-(4-fluorophenyl)-1-piperazinyl]methyl]-2,3-dihydro-2-oxo-1H-imidazole-4-carboxylate.
5-[[4-(3-Bromophenyl)-1-piperazinyl]methyl]-2,3-dihydro-N-phenyl-2-oxo-1H-imidazole-4-carboxamide.
5-[[4-(2-Methylphenyl)-1-piperazinyl]methyl]-2,3-dihydro-2-oxo-1H-imidazole-4-carboxamide.
Ethyl 2,3-dihydro-5-[(4-ethyl-1-piperazinyl)methyl]-2-oxo-1H-imidazole-4-carboxylate.
Ethyl 2,3-dihydro-5-[1-[4-(2-methylphenyl)-1-piperazinyl]ethyl]-2-oxo-1H-imidazole-4-carboxylate.

Ethyl 2,3-dihydro-5-[(dipropylamino)methyl]-2-oxo-1H-imidazole-4-carboxylate.

2,3-Dihydro-5-(methoxycarbonyl)-N,N,N-triethyl-2-oxo-1H-imidazole-4-methanaminium bromide.

1-[[2,3-Dihydro-5-(ethoxycarbonyl)-2-oxo-1H-imidazol-4-yl]methyl]pyridinium chloride.

Ethyl 2,3-dipropionyl-2,3-dihydro-5-[[4-(2-methylphenyl)-1-piperazinyl]methyl]-2-oxo-1H-imidazole-4-carboxylate.

Ethyl 1,3-dibenzoyl-2,3-dihydro-5-[[4-(2-methylphenyl)-1-piperazinyl]methyl]-2-oxo-1H-imidazole-4-carboxylate.

Ethyl 2,3-Dihydro-1,3-diethyl-5-[[4-(2-methylphenyl)-1-piperazinyl]methyl]-2-oxo-1H-imidazole-4-carboxylate.

To obtain the compounds of the present invention, a 1,3-diacetyl imidazolone such as a compound of the formula:

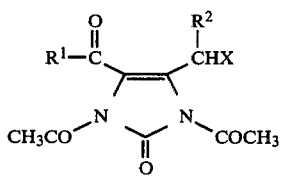

wherein X is hydrogen is brominated to give the corresponding compound wherein X is Br. The reaction is carried out using N-bromosuccinimide in the presence of a free radical initiator such as benzoyl peroxide in an appropriate solvent such as carbon tetrachloride. The specific diacetyl starting materials are obtained from the corresponding 1,3-unsubstituted imidazolone by acetylation with acetyl chloride or acetic anhydride. When $R^1$ is alkoxy, the starting ester is obtained by the procedure described by Duschinsky and Dolan, *J. Am. Chem. Soc.*, 68, 2350 (1946). When $R^1$ contains an amino group, the imidazole-4-carboxamide is obtained from the appropriate N-substituted 2-(hydroxyimino)-3-oxobutanamide which is reduced to the corresponding 2-amino compound, either catalytically or chemically, depending on the amide involved. The resulting 2-amino compound, is then reacted with potassium cyanate to produce the imidazolecarboxamide.

The bromo compounds obtained above can be treated with hydrobromic acid in acetic acid to remove one or both of the N-acetyl groups. The resulting imidazolone is then treated with the appropriate amine to give the desired compounds of the present invention. If pyridine or an appropriate tertiary amine is used in the reaction, the process gives, directly, the quarternary ammonium compounds of the present invention.

Although the present process has been described using 1,3-unsubstituted imidazolones, it is also possible to use the corresponding 1,3-diacetyl compounds or similarly substituted compounds but, when such compounds are used, the amine will also react with the acyl group to give the deacetylated imidazolone and an N-acyl amine. It is thus necessary to use an excess of the amine to allow for this reaction but this would not be a desirable process when the amine used is not readily available and inexpensive.

The compounds in which R represents lower alkanoyl or benzoyl are obtained by reaction of the compounds in which R represents hydrogen with an excess of the appropriate acid anhydride or acid chloride. The compounds wherein $R^1$ is hydroxy are obtained from the corresponding compounds wherein $R^1$ is alkoxy by alkaline hydrolysis, with lithium hydroxide in water being preferred for the process.

When the final product is obtained from any of the above reactions in the form of an acid addition salt, it can be readily converted to the corresponding free amine by standard procedures or, when the product is obtained as the free amine, it can be converted to the corresponding salt by standard procedures.

The compounds of the present invention can be used in the treatment of hypertension including primary or essential hypertension, hormonally induced hypertension, renal hypertension and chemically induced hypertension. The compounds of the present invention can also be used as anti-thrombotics. They affect the coagulation of blood by preventing the aggregation of blood platelets, which play a dominant role in thrombotic conditions both in the initial event and at the occlusive stage. Arterial thrombosis, particularly in arteries supplying the heart muscle and brain, is a leading cause of death and disability. In addition, the compounds of the present invention in which $-NR^3R^4$ contains a piperazine group can also be used in the treatment of cardiac failure including congestive heart failure, backward heart failure, forward heart failure, left ventricular heat failure, or right ventricular heart failure or in the treatment of any other condition which requires the strengthening of heat action with a cardiotonic. In many respects, these compounds possess digitalis-like action.

Antihypertensive activity for the present compounds was demonstrated using groups of 12 spontaneously hypertensive rats. Blood pressure was measured by a pressure cuff occluder around the base of the tails of the rats. The blood pressure was determined in the animals, test compound was administered orally in a vehicle at a dose of 50 mg/kg and blood pressure was measured again at 1, 2, 3, 4 and 24 hours after administration of the test compound. The difference in blood pressure observed was analyzed to establish if it was statistically significant. The vehicle used in administering the test compound did not have a significant effect on blood pressure when used alone.

Cardiotonic activity for the present compounds was demonstrated by the following procedure. A Walton-Brodie strain gage arch was surgically implanted on the heart of anesthetized dogs to measure cardiac contractile force. After the vital signs of the animal were stable for 10 minutes, test compound was administered intravenously starting at a dose of 0.3 mg/kg and continuing with higher doses of 1, 3 and 10 mg/kg if no effect is observed. Active compounds, such as compounds of the present invention, which increase cardiac contractile force measured in this way exert a true positive inotropic effect, or a cardiotonic effect.

Antithrombotic activity for the present compounds is demonstrated by the following procedure. When adenosine diphosphate is added to citrated platelet rich human plasma, a typical aggregation of blood platelets occurs. Antithrombotic activity is determined by adding a test compound to the citrated platelet rich human plasma in concentrations of 3, 10, 30 and 100 μg/ml and subsequently adding adenosine diphosphate and observing the extent of inhibition of aggregation of blood platelets.

The compounds may be administered in various manners to achieve the desired effect. The compounds may be administered alone or in the form of pharmaceutical preparations to the patient being treated either orally or parenterally, that is, intravenously or intramuscularly. The amount of compound administered will vary with the severity of the hypertension, cardiac failure or blood clotting and the mode of administration. For oral administration the antihypertensively effective amount of compound is from about 0.1 mg/kg (milligrams per kilograms) of patient body weight per day to about 100 mg/kg of patient body weight per day and preferably from about 5 mg/kg of patient body weight per day to about 30 mg/kg of patient body weight per day.

For parenteral administration the antihypertensively effective amount of compound is from about 0.01 mg/kg of patient body weight per day up to about 50 mg/kg of patient body weight per day and preferably from about 0.1 mg/kg of patient body weight per day up to about 20.0 mg/kg of patient body weight per day. For oral or parenteral administration the cardiotonically effective amount of compound is from about 0.1 mg/kg of patient body weight per day up to about 50 mg/kg of patient body weight per day and preferably from about 0.1 mg/kg of patient body weight per day up to about 20.0 mg/kg of patient body weight per day. For oral or parenteral administration the anticoagulant effective amount of compound is from about 0.1 mg/kg of patient body weight per day up to about 100 mg/kg of patient body weight per day and preferably from about 0.1 mg/kg of patient body weight per day up to about 50 mg/kg of patient body weight per day.

For oral administration a unit dosage may contain, for example, from 1 to 100 mg of the active ingredient. For parenteral administration a unit dosage may contain, for example, from 0.5 to 50 mg of the active ingredient. Repetitive daily administration of the compounds may be desired and will vary with the condition of the patient and the mode of administration.

As used herein the term patient is taken to mean a warm blooded animal, for example, birds, such as chickens and turkeys, and mammals, such as primates, humans, sheep, horses, bovine cows and bulls, pigs, dogs, cats, rats and mice.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of the invention can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol and glycols such as propylene glycol or polyethylene glycol can be used as liquid carriers for injectable solutions. Particularly preferred are combinations of the above carriers such as aqueous ethanol or propylene glycol-aqueous ethanol at alkaline pH.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradeable polymers or synthetic silicones, for example, Silastic, silicone rubber manufactured by the Dow-Corning Corporation.

Following are illustrative pharmaceutical formulations which may be employed in practicing the present invention:

|     |                                                                                                    | Per Tablet |
| --- | -------------------------------------------------------------------------------------------------- | ---------- |
|     | Preparation of a Tablet Formulation                                                                |            |
| (a) | Ethyl 2,3-dihydro-5-[[4-(2-methoxyphenyl)-1-piperazinyl]methyl]-2-oxo-1H—imidazole-4-carboxylate hydrochloride | 100 mg |
| (b) | Cornstarch                                                                                         | 15 mg      |
| (c) | Lactose                                                                                            | 33.5 mg    |
| (d) | Magnesium stearate                                                                                 | 1.5 mg     |
|     | Preparation of a Parenteral Formulation                                                            |            |
| (a) | Ethyl 2,3-dihydro-5-[[4-(2-methoxyphenyl)-1-piperazinyl]methyl]-2-oxo-1H—imidazole-4-carboxylate hydrochloride | 0.100 g |
| (b) | Sodium hydroxide                                                                                   | 0.025 g    |
| (c) | Ethanol                                                                                            | 1.516 g    |
| (d) | Propylene glycol                                                                                   | 8.264 g    |
| (e) | Water for injection qs ad                                                                          | 20.0 ml    |

The following examples are set forth to illustrate the preparation of compounds employed in the present invention but should not be construed as limiting it in any way.

EXAMPLE 1

A solution of 15.8 g of N,N-dimethyl-2-(hydroxyimino)-3-oxobutanamide in 400 ml of ethanol and 100 ml of 2 N hydrochloric acid is hydrogenated over 2 g of 5% palladium on charcoal catalyst in a Parr shaker until one molar equivalent of hydrogen is taken up (3–5 hours). The reaction mixture is then filtered to remove the catalyst and a solution of 16.2 g of potassium cyanate in 80 ml of water is added. The resulting solution is refluxed for 1 hour and then concentrated until solid crystallizes. The solid is separated by filtration and recrystallized from 50% aqueous ethanol to give 2,3-dihydro-N,N,5-trimethyl-2-oxo-1H-imidazole-4-carboxamide melting above 300° C.

If the above procedures is repeated using the appropriate substituted 2-(hydroxyimino)-3-oxobutanamide, the following compounds are obtained:

2,3-Dihydro-N,5-dimethyl-2-oxo-1H-imidazole-4-carboxamide melting above 300° C.

2,3-Dihydro-5-methyl-2-oxo-1H-imidazole-4-carboxamide melting above 300° C.

N-(tert-Butyl)-2,3-dihydro-5-methyl-2-oxo-1H-imidazole-4-carboxamide.

2,3-Dihydro-5-ethyl-N,N-dimethyl-2-oxo-1-H-imidazole-4-carboxamide.

EXAMPLE 2

To a stirred solution of 11.8 of 2-(hydroxyimino)-N-(4-methoxyphenyl)-3-oxobutanamide in 30 ml of acetic acid and 10 ml of acetic anhydride at 20°–30° C. is added 10 g of zinc dust and the mixture is stirred for 1 hour. Water (150 ml) is added, the mixture is stirred for 2 hours, and the zinc is removed by filtration. The solvent is evaporated from the filtrate under reduced pressure and the resulting residue is recrystallized from methanol to give 2-acetylamino-N-(4-methoxyphenyl)-3-oxobutanamide.

The product obtained in the preceding paragraph (10.6 g) is dissolved in 20 ml of 6 N hydrochloric acid and the solution is allowed to stand at room temperature for 5 minutes. A solution of 9.7 g of potassium cyanate in 80 ml of water is added and the mixture is stirred at room temperature for 16 hours. The precipitate which forms is separated by filtration and recrystallized twice from 50% aqueous ethanol to give 2,3-dihydro-N-(4-methoxyphenyl)-5-methyl-2-oxo-1H-imidazole-4-carboxamide melting at about 299°–301° C. (dec.).

If the above procedure is repeated using the appropriate N-substituted 2-(hydroxyimino)-3-oxobutanamide, the following compounds are obtained:

2,3-Dihydro-5-methyl-2-oxo-N-phenyl-1H-imidazole-4-carboxamide.
2,3-Dihydro-5-methyl-N-(2,4-dimethylphenyl)-2-oxo-1H-imidazole-4-carboxamide.
2,3-Dihydro-5-ethyl-2-oxo-N-phenyl-1H-imidazole-4-carboxamide.

EXAMPLE 3

A mixture of 54.5 g of ethyl 2,3-dihydro-5-methyl-2-oxo-1H-imidazole-4-carboxylate and 240 ml of acetic anhydride is refluxed for 13 hours. The mixture is distilled to remove 150 ml of acetic anhydride and acetic acid; this is replaced by fresh acetic anhydride and refluxing is resumed. After a total of 22 hours of reflux, excess acetic anhydride is evaporated under reduced pressure and the resulting residue is triturated with cyclohexane and then recrystallized from cyclohexane to give ethyl 1,3-diacetyl-2,3-dihydro-5-methyl-2-oxo-1H-imidazole-4-carboxylate melting at about 56°–58° C.

If the above procedure is repeated using acetic anhydride and the appropriate substituted 2,3-dihydro-2-oxo-1H-imidazole-4-carboxylic acid derivative, the following compounds are obtained:

1,3-Diacetyl-2,3-dihydro-N,N,5-trimethyl-2-oxo-1H-imidazole-4-carboxamide.
1,3-Diacetyl-2,3-dihydro-N,5-dimethyl-2-oxo-1H-imidazole-4-carboxamide.
1,3-Diacetyl-2,3-dihydro-5-methyl-2-oxo-1H-imidazole-4-carboxamide.
1,3-Diacetyl-N-(tert-butyl)-2,3-dihydro-5-methyl-2-oxo-1H-imidazole-4-carboxamide.
1,3-Diacetyl-2,3-dihydro-5-ethyl-N,N-dimethyl-2-oxo-1H-imidazole-4-carboxamide.
1,3-Diacetyl-2,3-dihydro-N-(4-methoxyphenyl)-5-methyl-2-oxo-1H-imidazole-4-carboxamide.
1,3-Diacetyl-2,3-dihydro-5-methyl-2-oxo-N-phenyl-1H-imidazole-4-carboxamide.
1,3-Diacetyl-2,3-dihydro-5-methyl-N-(2,4-dimethylphenyl)-2-oxo-1H-imidazole-4-carboxamide.
1,3-Diacetyl-2,3-dihydro-5-ethyl-2-oxo-N-phenyl-1H-imidazole-4-carboxamide.

EXAMPLE 4

A mixture of 12.7 g (0.050 mole) of ethyl 1,3-diacetyl-2,3-dihydro-5-methyl-2-oxo-1H-imidazole-4-carboxylate, 9.3 g (0.052 mole) of N-bromosuccinimide and about 100 mg of benzoyl peroxide in 400 ml of carbon tetrachloride is stirred at reflux temperature for 4 hours. The mixture is then cooled and filtered to remove the succinimide which formed. The solvent is evaporated from the filtrate to give 5-(bromomethyl)-1,3-diacetyl-2,3-dihydro-2-oxo-1H-imidazole-4-carboxylate as an oil.

If the above procedure is repeated using N-bromosuccinimide and the appropriate substituted 1,3-diacetyl-2,3-dihydro-2-oxo-1H-imidazole-4-carboxylic acid derivative, the following compounds are obtained:

5-(Bromomethyl)-1,3-diacetyl-2,3-dihydro-N,N-dimethyl-2-oxo-1H-imidazole-4-carboxamide.
5-(Bromomethyl)-1,3-diacetyl-2,3-dihydro-N-methyl-2-oxo-1H-imidazole-4-carboxamide.
5-(Bromomethyl)-1,3-diacetyl-2,3-dihydro-2-oxo-1H-imidazole-4-carboxamide.
5-(Bromomethyl)-N-(tert-butyl)-1,3-diacetyl-2,3-dihydro-2-oxo-1H-imidazole-4-carboxamide.
5-(1-Bromomethyl)-2,3-dihydro-1,3-diacetyl-N,N-dimethyl-2-oxo-1H-imidazole-4-carboxamide.
5-(Bromomethyl)-1,3-diacetyl-2,3-dihydro-N-(4-methoxyphenyl)-2-oxo-1H-imidazole-4-carboxamide.
5-(Bromomethyl)-1,3-diacetyl-2,3-dihydro-2-oxo-N-phenyl-1H-imidazole-4carboxamide.
5-(Bromomethyl)-1,3-diacetyl-2,3-dihydro-N-(2,4-dimethylphenyl)-2-oxo-1H-imidazole-4-carboxamide.
5-(1-Bromoethyl)-1,3-diacetyl-2,3-dihydro-2-oxo-N-phenyl-1H-imidazole-4-carboxamide.
Ethyl 5-(bromomethyl)-2,3-dihydro-1,3-dimethyl-2-oxo-1H-imidazole-4-carboxylate.

EXAMPLE 5

Crude ethyl 5-(bromomethyl)-1,3-diacetyl-2,3-dihydro-2-oxo-1H-imidazole-4-carboxylate is dissolved in 30% hydrobromic acid in acetic acid and the solution is allowed to stand at room temperature for 4 hours. The solid which precipitates is separated by filtration and dried in vacuo at 80° C. over potassium hydroxide to give ethyl 3-acetyl-5-(bromomethyl)-2,3-dihydro-2-oxo-1H-imidazole-4-carboxylate melting at about 193°–194° C. (dec.).

If the above procedure is repeated using the appropriate substituted 1,3-diacetyl-2,3-dihydro-2-oxo-1H-imidazole-4-carboxylic acid derivative, the following compounds are obtained:

5-(Bromomethyl)-2,3-dihydro-N,N-dimethyl-2-oxo-1H-imidazole-4-carboxamide.
5-(Bromomethyl)-2,3-dihydro-N-methyl-2-oxo-1H-imidazole-4-carboxamide.
5-(Bromomethyl)-2,3-dihydro-2-oxo-1H-imidazole-4-carboxamide.
5-(Bromomethyl)-N-(tert-butyl)-2,3-dihydro-2-oxo-1H-imidazole-4-carboxamide.
5-(1-Bromoethyl)-2,3-dihydro-N,N-dimethyl-2-oxo-1H-imidazole-4-carboxamide.
5-(Bromomethyl)-2,3-dihydro-N-(4-methoxyphenyl)-2-oxo-1H-imidazole-4-carboxamide.
5-(Bromomethyl)-2,3-dihydro-2-oxo-N-phenyl-1H-imidazole-4-carboxamide.
5-(Bromomethyl)-2,3-dihydro-N-(2,4-dimethylphenyl)-2-oxo-1H-imidazole-4-carboxamide.
5-(1-Bromoethyl)-2,3-dihydro-2-oxo-N-phenyl-1H-imidazole-4-carboxamide.

EXAMPLE 6

To a cooled solution (0° C.) of 2 g of 1-(2-methoxyphenyl)piperazine and 2.1 g of triethylamine in 40 ml of ethanol is added 2.9 g of ethyl 3-acetyl-5-(bromomethyl)-2,3-dihydro-2-oxo-1H-imidazole-4-carboxylate. The resulting solution is stirred at 0° C. for 4 hours, 30 ml of ice-water is added and the mixture is filtered. One equivalent of hydrochloric acid is added to the filtrate and it is evaporated to dryness. The residue crystallizes from a mixture of ethanol and ethyl acetate (1:1) and is recrystallized from that solvent mixture to give ethyl 2,3-dihydro-5-[[4-(2-methoxyphenyl)-1-piperazinyl]methyl]-2-oxo-1H-imidazole-4-carboxylate hydrochloride melting at about 227° C. (dec.). The free base of this compound has the following structural formula:

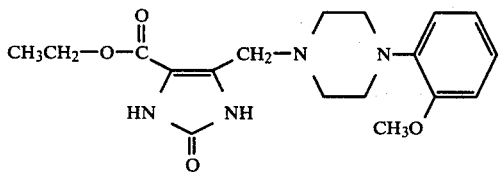

EXAMPLE 7

If 1-(2-methoxyphenyl)piperazine is reacted with 5-(bromomethyl)-2,3-dihydro-N,N-dimethyl-2-oxo-1H-imidazole-4-carboxamide and similar compounds according to the procedure of Example 6, the following compounds are obtained:

2,3-Dihydro-N,N-dimethyl-5-[[4-(2-methoxyphenyl)-1-piperazinyl]methyl]-2-oxo-1H-imidazole-4-carboxamide hydrochloride.

2,3-Dihydro-5-[[4-(2-methoxyphenyl)-1-piperazinyl]methyl]-N-methyl-2-oxo-1H-imidazole-4-carboxamide hydrochloride.

2,3-Dihydro-5-[[4-(2-methoxyphenyl)-1-piperazinyl]methyl]-2-oxo-1H-imidazole-4-carboxamide hydrochloride.

N-(tert-butyl)-2,3-dihydro-5-[[4-(2-methoxyphenyl)-1-piperazinyl]methyl]-2-oxo-1H-imidazole-4-carboxamide hydrochloride.

2,3-Dihydro-N,N-dimethyl-5-[1-[4-(2-methoxyphenyl)-1-piperazinyl]ethyl]2-oxo-1H-imidazole-4-carboxamide hydrochloride.

2,3-Dihydro-N-(4-methoxyphenyl)-5-[[4-(2-methoxyphenyl)-1-piperazinyl]methyl]-2-oxo-1H-imidazole-4-carboxamide hydrochloride.

2,3-Dihydro-5-[[4-(2-methoxyphenyl)-1-piperazinyl]methyl]-N-phenyl-2-oxo-1H-imidazole-4-carboxamide hydrochloride.

2,3-Dihydro-N-(2,4-dimethylphenyl)-5-[[4-(2-methoxyphenyl)-1-piperazinyl]methyl]-2-oxo-1H-imidazole-4-carboxamide hydrochloride.

2,3-Dihydro-5-[1-[4-(2-methoxyphenyl)-1-piperazinyl]ethyl]-N-phenyl-2-oxo-1H-imidazole-4-carboxamide hydrochloride.

Ethyl 2,3-dihydro-1,3-dimethyl-5-[[4-(2-methoxphenyl)-1-piperazinyl]methyl]-2-oxo-1H-imidazole-4-carboxylate hydrochloride.

EXAMPLE 8

If the procedure of Example 6 is repeated using ethyl 3-acetyl-5-(bromomethyl)-2,3-dihydro-2-oxo-1H-imidazole-4-carboxylate and the appropriate secondary amine, the following compounds are obtained:

Ethyl 5-[(dimethylamino)methyl]-2,3-dihydro-2-oxo-1H-imidazole-4-carboxylate hydrochloride.

Ethyl 5-[(diethylamino)methyl]-2,3-dihydro-2-oxo-1H-imidazole-4-carboxylate hydrochloride.

Ethyl 2,3-dihydro-2-oxo-5-[(1-pyrrolidinyl)methyl]-1H-imidazole-4-carboxylate hydrochloride.

Ethyl 2,3-dihydro-2-oxo-5-[(1-piperidinyl)]-1H-imidazole-4-carboxylate hydrochloride.

Ethyl 2,3-dihydro-5-[(4-morpholinyl)methyl]-2-oxo-1H-imidazole-4-carboxylate hydrochloride.

Ethyl 2,3-dihydro-5-[(4-methyl-piperazinyl)methyl]-2-oxo-1H-imidazole-4-carboxylate hydrochloride.

Ethyl 5-[[4-(4-chlorophenyl)-1-piperazinyl]methyl]-2,3-dihydro-2-oxo-1H-imidazole-4-carboxylate hydrochloride.

Ethyl 2,3-dihydro-5-[[4-(2-methylphenyl)-1-piperazinyl]methyl]-oxo-1H-imidazole-4-carboxylate hydrochloride.

Ethyl 2,3-dihydro-5-[[4-(3-trifluoromethylphenyl)-1-piperazinyl]methyl]-2-oxo-1H-imidazole-4-carboxylate hydrochloride.

EXAMPLE 9

The ethyl 2,3-dihydro-5-[[4-(2-methoxyphenyl)-1-piperazinyl]methyl]-2-oxo-1H-imidazole-4-carboxylate obtained in Example 6 is dissolved in a solution of 3 equivalents of lithium hydroxide in water. The solution is allowed to stand at room temperature for 48 hours before it is neutralized carefully with 2 equivalents of hydrochloric acid. The precipitate which forms is separated by filtration and recrystallized from a mixture of ethanol and ethyl acetate to give 2,3-dihydro-5-[[4-(2-methoxyphenyl)-1-piperazinyl]methyl]-2-oxo-1H-imidazole-4-carboxylic acid.

EXAMPLE 10

To a solution of 10.4 g of crude ethyl 5-(bromomethyl)-1,3-diacetyl-2,3-dihydro-2-oxo-1H-imidazole-4-carboxylate in 100 ml of dry tetrahydrofuran, cooled in an ice bath under argon, there is added gaseous trimethylamine for 7 minutes. The mixture is stirred at 0° C. for 15 minutes and then evaporated to dryness. To the residue is added 50 ml of 31% hydrogen bromide in acetic acid and the mixture is warmed briefly on a steam bath to about 50° C. to bring about dissolution. It is then allowed to stand at room temperature for 1 hour before it is evaporated to dryness. Water (50 ml) is added to the residue and the resultant aqueous mixture is washed with methylene chloride, treated with charcoal, filtered through diatomaceous earth, and evaporated to dryness. The resultant residue is crystallized from a mixture of ethanol and ethyl acetate (1:3) and then recrystallized from ethanol to give 5-(ethoxycarbonyl)-2,3-dihydro-N,N,N-trimethyl-2-oxo-1H-imidazole-4-methanaminium bromide monohydrate melting at about 199°–200° C. (dec.). This compound has the following structural formula:

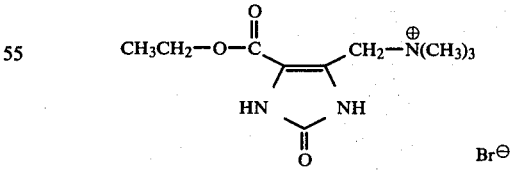

EXAMPLE 11

The sodium salt of ethyl 2,3-dihydro-5-methyl-2-oxo-1H-imidazole-4-carboxylate is prepared from 4.9 g of ethyl 2,3-dihydro-5-methyl-2-oxo-1H-imidazole-4-carboxylate in 100 ml of methanol with the addition of 1.6 g of sodium methoxide. A mixture is prepared from 8.0 g of this sodium salt, 120 ml of dimethylsulfoxide and 19.5 g of methyl iodide. This mixture is stirred at room temperature for 60 minutes and then poured into 800 ml of water. The resulting mixture is then extracted with methylene chloride and the solvent is evaporated from the extract to give ethyl 2,3;1-dihydro-1,3,5-trimethyl-2-oxo-1H-imidazole-4-carboxylate.

What is claimed is:

1. A compound of the formula:

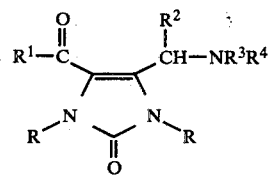

wherein R is hydrogen, lower alkyl of 1–4 C, lower alkanoyl of 2–4 C, or benzoyl; $R^1$ is hydroxy, lower alkoxy of 1–4 C, amino, (lower alkyl)amino, (lower alkyl)$_2$amino or —NHR$_5$ wherein R$_5$ is phenyl, methylphenyl, dimethylphenyl or methoxyphenyl; $R^2$ is hydrogen or lower alkyl of 1–4 C; and —NR$^3$R$^4$ is

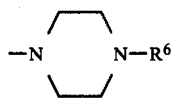

wherein $R^6$ is lower alkyl of 1–4 C, phenyl, halophenyl, methylphenyl, methoxyphenyl or trifluoromethylphenyl; and the pharmaceutically acceptable acid addition salts and the lower alkyl quaternary ammonium salts of the aforesaid compounds.

2. A compound according to claim 1 which has the formula:

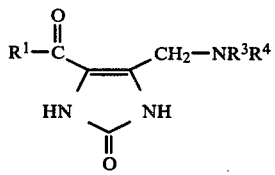

wherein $R^1$ is hydroxy, lower alkoxy of 1–4 C, amino, (lower alkyl)amino, (lower alkyl)$_2$amino or —NHR$_5$ wherein R$_5$ is phenyl, methylphenyl, dimethylphenyl or methoxyphenyl; and —NR$^3$R$^4$ is

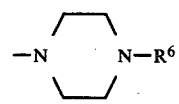

wherein $R^6$ is lower alkyl of 1–4 C, phenyl, halophenyl, methylphenyl, methoxyphenyl or trifluoromethylphenyl.

3. A compound according to claim 1 which has the formula:

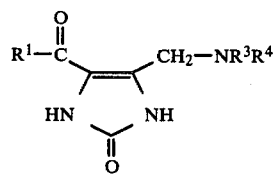

wherein $R^1$ is lower alkoxy of 1–4 C, —NR$^3$R$^4$ is

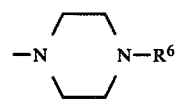

wherein $R^6$ is lower alkyl of 1–4 C, phenyl, halophenyl, methylphenyl, methoxyphenyl or trifluoromethylphenyl.

4. A compound according to claim 1 which has the formula:

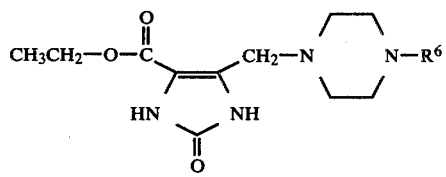

wherein $R^6$ is lower alkyl of 1–4 C, phenyl, halophenyl, methylphenyl, methoxyphenyl or trifluoromethylphenyl.

5. A compound according to claim 1 which is ethyl 2,3-dihydro-5-[[4-(2-methoxyphenyl)-1-piperazinyl]methyl]-2-oxo-1H-imidazole-4-carboxylate.

* * * * *